United States Patent
Umlauft et al.

(10) Patent No.: US 9,316,606 B2
(45) Date of Patent: Apr. 19, 2016

(54) SENSORS FOR LAYOUT VALIDATION OF AN OXYGEN MODULE

(71) Applicant: AIRBUS OPERATIONS GMBH, Hamburg (DE)

(72) Inventors: Sebastian Umlauft, Hamburg (DE); Tobias Ameling, Hamburg (DE); Nino-Ninov Penkov, Hamburg (DE); Andreas Hottenrott, Hamburg (DE)

(73) Assignee: AIRBUS OPERATIONS GMBH, Hamburg (DE)

( * ) Notice: Subject to any disclaimer, the term of this patent is extended or adjusted under 35 U.S.C. 154(b) by 415 days.

(21) Appl. No.: 13/869,526

(22) Filed: Apr. 24, 2013

(65) Prior Publication Data

US 2013/0305810 A1   Nov. 21, 2013

Related U.S. Application Data

(60) Provisional application No. 61/637,873, filed on Apr. 25, 2012.

(30) Foreign Application Priority Data

Apr. 25, 2012 (DE) .................. 10 2012 008 266

(51) Int. Cl.
   *G01N 27/04* (2006.01)
   *B64D 11/00* (2006.01)

(52) U.S. Cl.
   CPC .............. *G01N 27/04* (2013.01); *B64D 11/00* (2013.01); *B64D 2231/025* (2013.01)

(58) Field of Classification Search
   CPC ........... G01N 27/04; B65D 13/00; A62B 7/14
   See application file for complete search history.

(56) References Cited

U.S. PATENT DOCUMENTS

| 5,074,053 | A | * | 12/1991 | West ........................... 33/708 |
| 5,798,640 | A | * | 8/1998 | Gier et al. ............... 324/207.24 |
| 6,070,337 | A | * | 6/2000 | Wallrafen ..................... 33/708 |
| 2002/0144938 | A1 | | 10/2002 | Hawkins |
| 2012/0032027 | A1 | | 2/2012 | Gehm |
| 2012/0312921 | A1 | * | 12/2012 | Grosse-Plankermann et al. ............ 244/118.5 |
| 2013/0149950 | A1 | | 6/2013 | Umlauft |

FOREIGN PATENT DOCUMENTS

| DE | 20 2006 013 815 | 2/2007 |
| DE | 10 2009 018 111 | 10/2010 |
| DE | 10 2010 018 569 | 11/2011 |

OTHER PUBLICATIONS

German Search Report dated Jun. 20, 2013.
German Office Action dated Aug. 14, 2015.

* cited by examiner

*Primary Examiner* — Hezron E Williams
*Assistant Examiner* — David Z Huang
(74) *Attorney, Agent, or Firm* — Dickinson Wright PLLC

(57) ABSTRACT

A sensor device for an oxygen module mountable on board an aircraft includes an electrical conducting element, a defining device for defining at least one measurement section, assigned to the oxygen module, on the electrical conducting element, and an evaluating unit for determining an electrical resistance present along the at least one measurement section, the evaluating unit further being configured to ascertain, based on the determined electrical resistance, whether the oxygen module is present. An aircraft has at least one oxygen module mounted on board the aircraft and at least one sensor device of the above type.

15 Claims, 10 Drawing Sheets

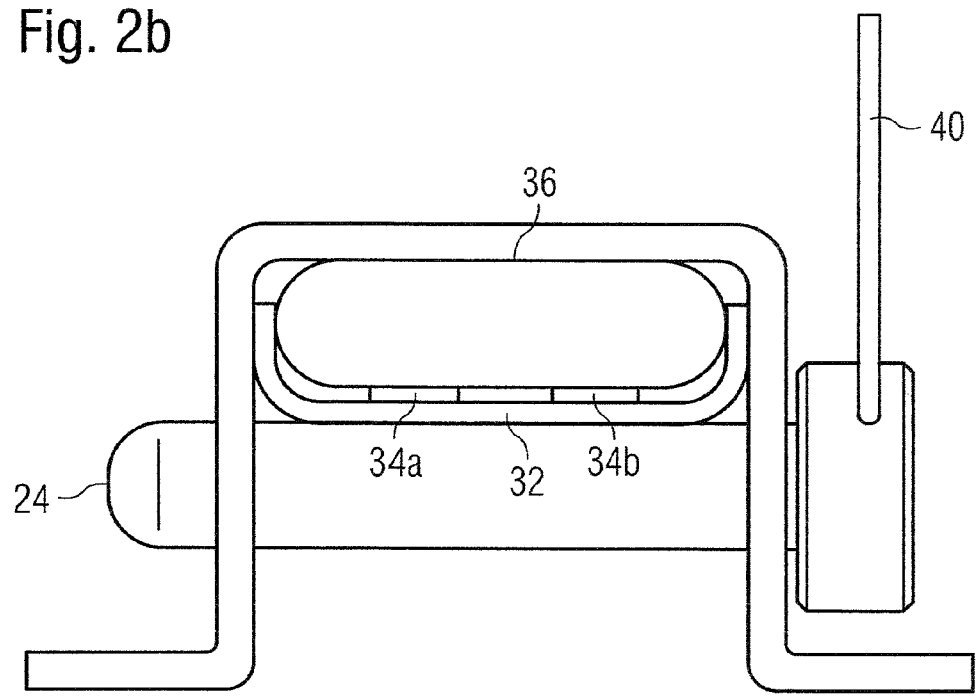

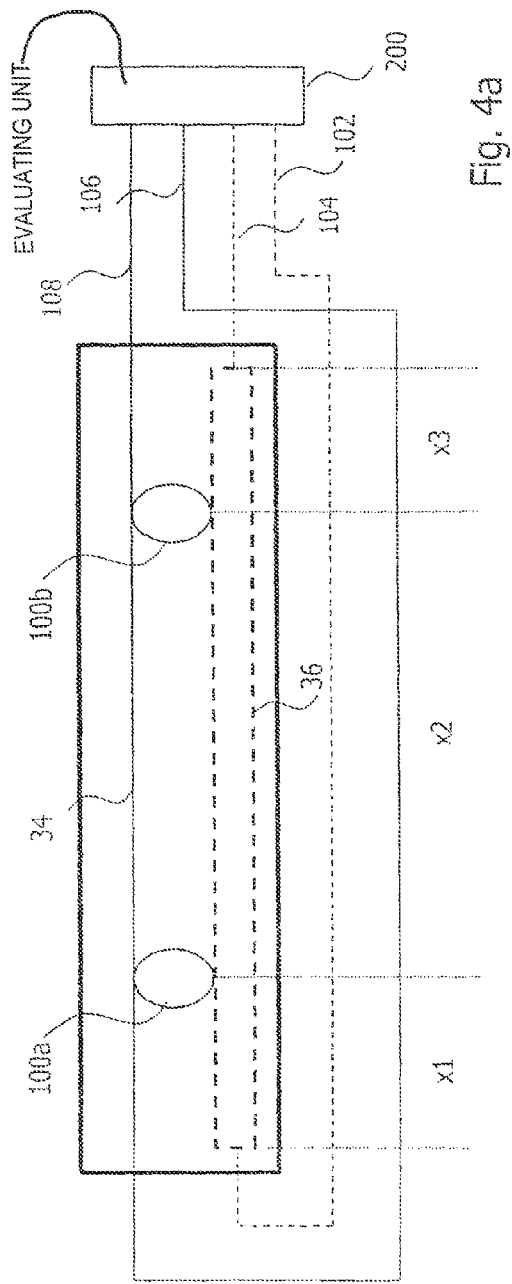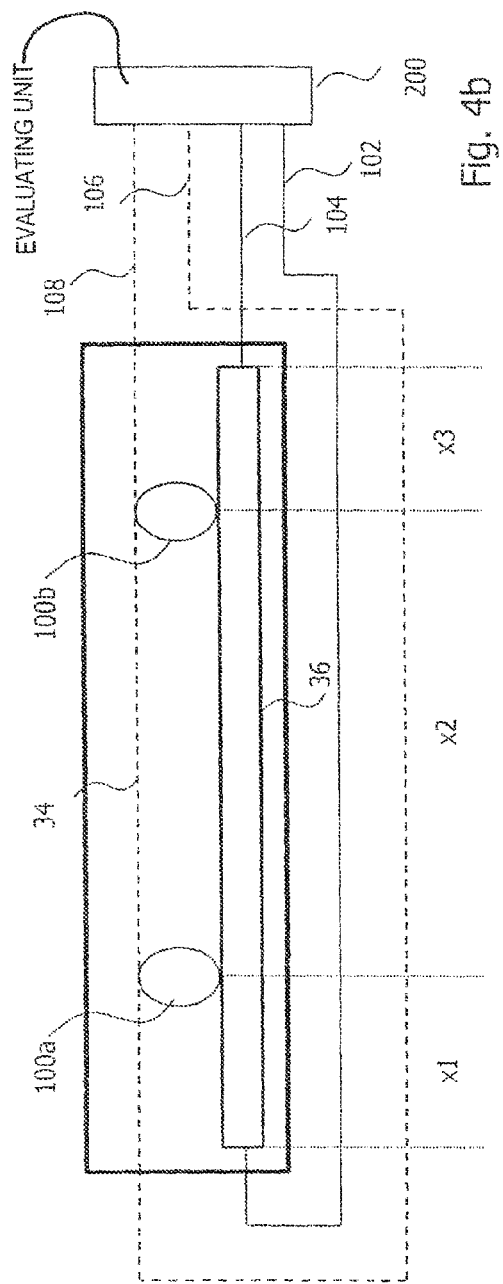

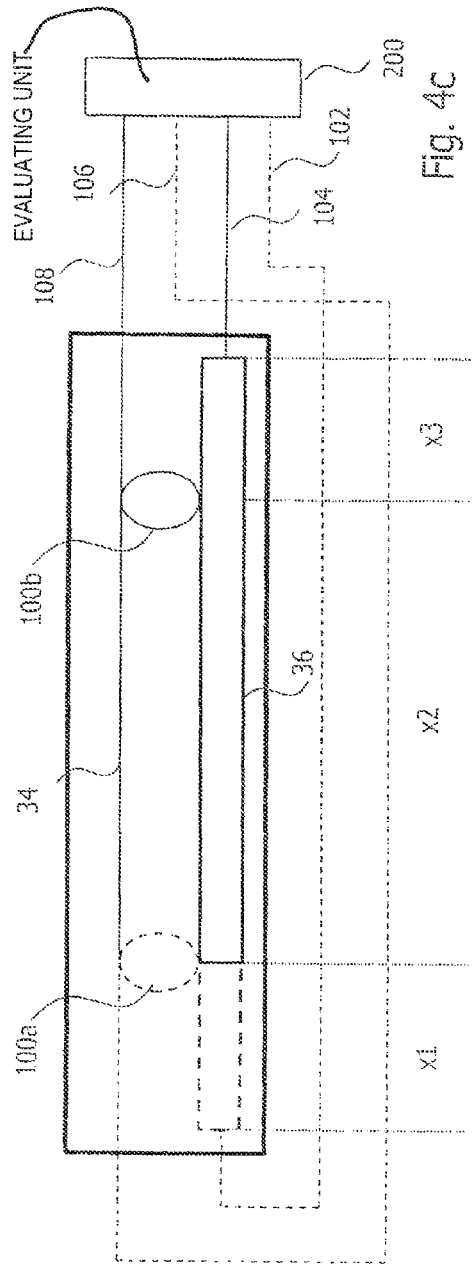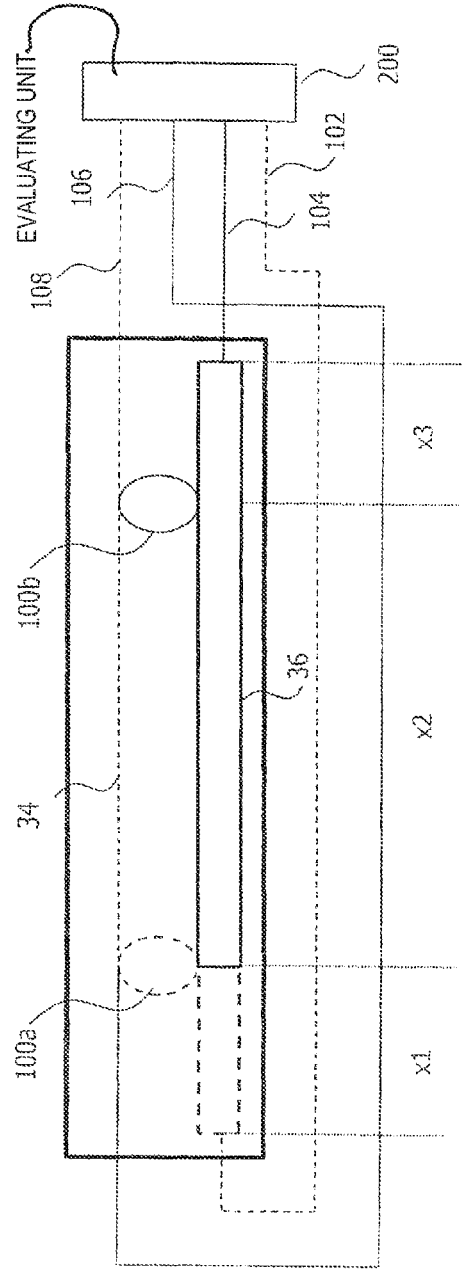

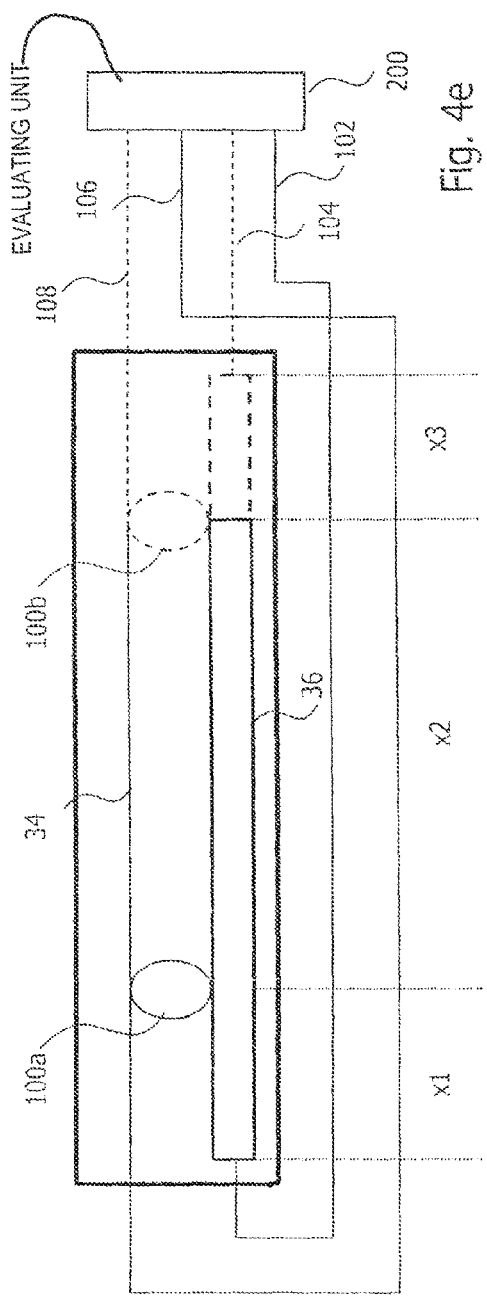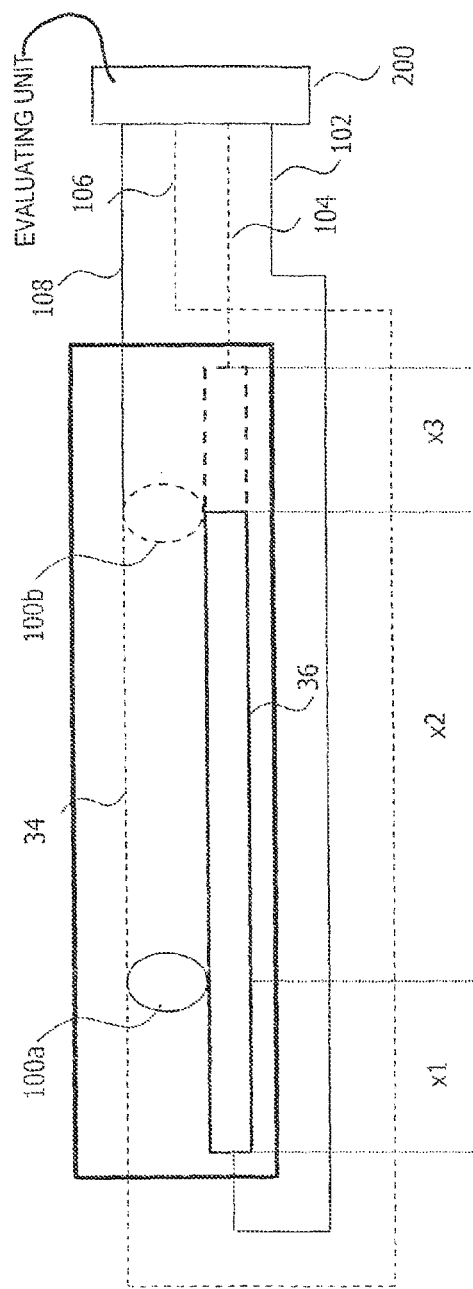

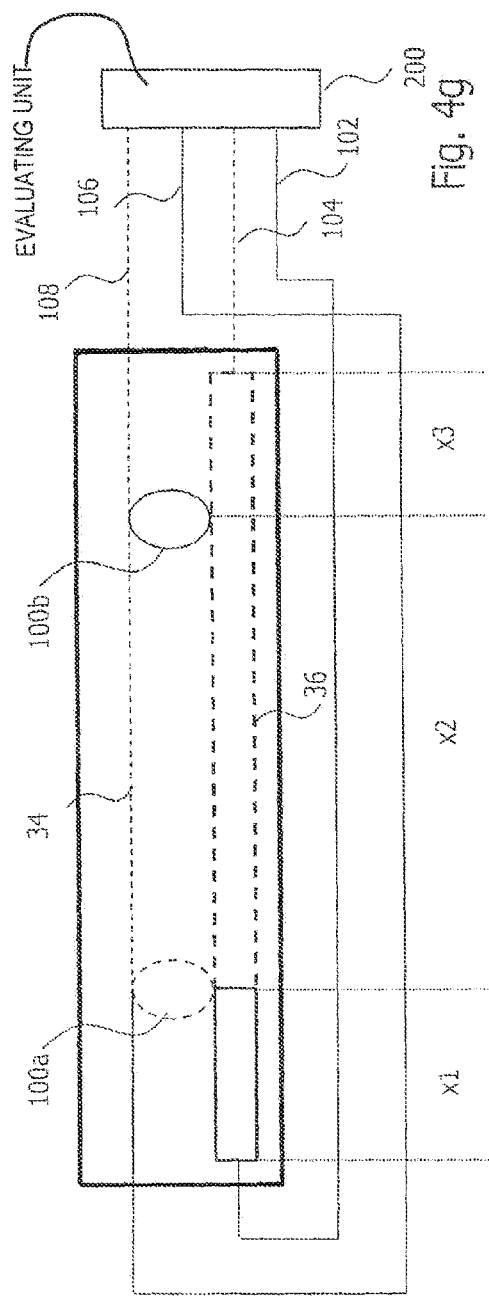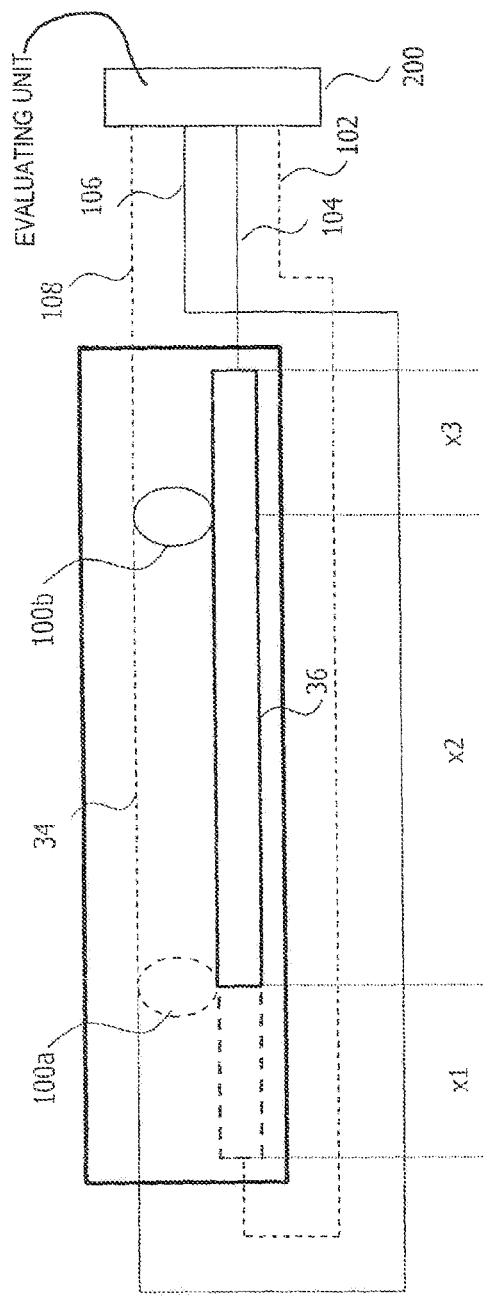

SENSORS FOR LAYOUT VALIDATION OF AN OXYGEN MODULE

CROSS REFERENCE TO RELATED APPLICATIONS

This application is entitled to and claims the benefit of German Application No. DE 10 2012 008 266.5 filed Apr. 25, 2012 and U.S. Provisional Application No. 61/637,873, filed Apr. 25, 2012, the disclosures of each of which, including the specification, claims, drawings and abstract, are incorporated herein by reference in their entirety.

FIELD

The present invention relates to a sensor device for an oxygen module mountable on board an aircraft and to an aircraft having at least one oxygen module mounted on board the aircraft and at least one sensor device of this type.

BACKGROUND

In conventional cabin architectures of aircraft, the seats and accordingly also the seat rows are arranged at fixed seat positions, i.e. aircraft usually have a fixed cabin architecture. To each seat row there is usually assigned a respective oxygen module. Accordingly, each of the oxygen modules is normally arranged and installed above the seat row assigned to it. For this purpose, the oxygen modules are normally connected to a supply duct extending in the aircraft.

In order to be able to carry more or fewer passengers, if required, in subregions of the aircraft cabin or the entire aircraft cabin, increasingly a more flexible cabin layout is sought. For this purpose, the seats may be displaced to increase or decrease the seat spacing in the longitudinal direction of the aircraft. In order to ensure the correct assignment between oxygen module and seat row, it is desirable for all the required oxygen modules to be installed on board the aircraft. To check the correct layout of the variable cabin architecture, it is desirable to ascertain whether each oxygen module is situated at the respectively correct position (in the longitudinal direction of the aircraft) above the seat row assigned to it.

SUMMARY

It is an object of the present invention to provide a sensor device and an aircraft having at least one such sensor device, it being possible by means of the sensor device to reliably determine in a simple manner whether oxygen modules mountable on board the aircraft are installed.

This object is achieved by the subject matter of attached claims. Specific embodiments emerge in each case from the dependent claims.

According to a first aspect, a sensor device for an oxygen module mountable on board an aircraft is provided. The sensor device comprises an electrical conducting element, a defining device and an evaluating unit. The defining device is configured to define at least one measurement section, assigned to the oxygen module, on the electrical conducting element. The evaluating unit is configured to determine an electrical resistance present along the at least one measurement section. Furthermore, the evaluating unit is configured to ascertain, based on the determined electrical resistance, whether the oxygen module is present, for example is correctly fitted and installed.

The electrical conducting element may comprise an electrical conductor, such as, for example, an electrically conductive wire. It is, for example, conceivable that the electrical conductor, such as the electrical conductive wire, is wound in the form of a coil and comprises a multiplicity of turns. The electrical conducting element may be connectable or connected at both of its ends to a voltage source and be supplied with a voltage via the latter, in order to carry an electric current.

The defining device is configured to define on the electrical conducting element, for example on the electrical conductor, such as the electrically conductive wire, a measurement section at which the associated resistance is to be measured (on application of a predetermined voltage). For defining the measurement section, for example a first (fixed) measurement point may be predetermined and the defining device may define at least one second (variable) measurement point and hence the measurement section. The first measurement point may, for example, be the beginning or the end of the electrical conductor. The at least one second measurement point may be any desired point along the electrical conductor. For example, the at least one second measurement point may be assigned to the oxygen module, for example the position of the oxygen module in the longitudinal direction of the aircraft. Accordingly, the measurement section may be the region of the electrical conductor extending between the first and the at least one second measurement point.

It is, however, also conceivable that two or more measurement points are defined by the defining device and accordingly the measurement section is defined by these two or more measurement points. The electrical resistance present along this defined measurement section can then be determined by the evaluating unit. For example, the evaluating unit may have an ohmmeter component which can directly measure the electrical resistance along the measurement section. It is, however, also conceivable that the evaluating unit can determine the resistance value based on a measured current and a voltage applied and thereby known to the evaluating unit.

The defined measurement section may be a continuous section along the electrical conductor between the first and the second measurement point. It is, however, also conceivable that the defined measurement section is composed of two or more measurement subsections along the electrical conductor. It is, for example, conceivable that a first measurement subsection runs from the first measurement point to the second measurement point along the electrical conductor, a second measurement subsection runs from a third measurement point to a fourth measurement point along the electrical conductor, etc.

Based on the determined electrical resistance, the evaluating unit can infer whether the oxygen module is present, e.g. correctly installed.

For example, the evaluating unit may be configured to compare the determined electrical resistance with a predetermined reference resistance and from the comparison derive whether the oxygen module is present. For example, the evaluating unit may be configured to ascertain that the oxygen module is present when the determined electrical resistance is less than a predetermined reference resistance, for example by at least a preset deviation from the predetermined reference resistance. The reference resistance may, for example, be the electrical resistance along a preset section of the electrical conductor or the electrical resistance along the entire electrical conductor.

Since the oxygen module is assigned to the measurement section, the evaluating unit can, for example, only ascertain a deviation between the determined electrical resistance and the predetermined reference resistance, such as, for example, ascertain that the determined electrical resistance is less than the predetermined reference resistance (for example by at least a preset deviation), when an oxygen module is present at all, for example is installed. The assignment may be effected via a physical connection, e.g. in the form of a string, cord or lanyard connection, between the sensor device and the oxygen module. It is conceivable that, only when the physical connection between sensor device and oxygen module exists, does the defining device define the measurement section and accordingly only then is a deviation of the measured electrical resistance from the predetermined reference resistance ascertainable. By contrast, if no deviation from the reference resistance is ascertained, the evaluating unit can infer that the oxygen module is not installed.

Through the resistance measurement, it is therefore reliably determined in a simple manner whether the oxygen module is present.

Furthermore, with the aid of the sensor device, it is possible to determine the position of the oxygen module, e.g. the position of the oxygen module in the longitudinal direction of the aircraft or the position of the oxygen module with respect to a supply duct extending in the longitudinal direction of the aircraft. For this purpose, the evaluating unit may be configured to derive the position of the oxygen module by comparing the determined electrical resistance with the reference resistance. For example, the evaluating unit may derive the position of the oxygen module from the quotient between the determined electrical resistance and the reference resistance. The reference resistance may, for example, be previously known to the evaluating unit or be firstly predetermined, e.g. in a calibrating operation, by the evaluating unit. The reference resistance may be the electrical resistance along the entire length of the electrical conducting element. If now a section of the electrical conducting element is defined as the measurement section, the evaluating unit can infer the length of the subsection from the multiplication of the length, assigned to the reference resistance, of the electrical conductor (which may, for example, be stored in the evaluating unit) by the quotient of the determined electrical resistance along the measurement section and the resistance along the entire section (the quotient results from the rule of three method). The length l of an electrical conductor can be calculated from the following formula:

$$R = \frac{l}{A} * \rho$$
$$=> l$$
$$= \frac{R * A}{\rho}$$

In the above formula, R denotes the electrical resistance of the electrical conductor, A denotes the cross-sectional area of the electrical conductor and $\rho$ denotes the resistivity (material constant) of the electrical conductor.

This gives for the length l1 of the measurement section $$l1 = \frac{R1}{R2} * l2$$

where R1 denotes the determined electrical resistance of the measurement section, R2 denotes the reference resistance (e.g. the electrical resistance on the entire electrical conductor) and l2 denotes the length of the electrical conductor assigned to the reference resistance (e.g. the length of the entire electrical conductor).

As already stated above, the defining device may define two or more measurement subsections, the electrical resistances of which are accordingly added up, so that the total resistance present on the measurement section (which is formed by these measurement subsections) can be compared with the reference resistance. The above-mentioned formulae enable the evaluating unit to determine the resistance and the length of the measurement section, irrespective of whether the measurement section is composed of only one, of two or more than two measurement subsections. Since the oxygen module is assigned to the measurement section, the evaluating unit can infer the position of the oxygen module in the longitudinal direction of the aircraft from the length of the measurement section. For example, the position of the oxygen module in the longitudinal direction of the aircraft may correlate with or be related to the length of the measurement section. As one possible simple configuration, it is conceivable that the measurement section is defined by the beginning of the electrical conductor (as the first measurement point) and a second measurement point, defined by the defining device, along the electrical conductor, the second measurement point being related to the position of the oxygen module in the longitudinal direction of the aircraft. For example, the position of the second measurement point in the longitudinal direction of the aircraft corresponds to the position of the oxygen module in the longitudinal direction of the aircraft, i.e. it is possible that the second measurement point is defined at the position at which the oxygen module is arranged. Both for the position of the oxygen module and for the second measurement point, the first measurement point may in this case represent the reference point (e.g. the zero point) for the length calculation. This simple configuration is, however, to be understood as being purely by way of example, i.e. other configurations are also conceivable in which e.g. two or more measurement points are flexibly defined, two or more measurement subsections are defined or the like.

Through the comparison of the electrical resistance of the measurement section with the reference resistance, it is possible to reliably determine the position of the oxygen module in a simple manner.

The defining device may comprise a contacting device for contacting the electrical conducting element, for example the electrical conductor of the electrical conducting element, at at least one contacting location, the at least one contacting location being assigned to the oxygen module and defining the at least one measurement section on the electrical conducting element. For example, the at least one contacting location may correspond to the at least one second (flexible) measurement point and thereby, as described above, define the at least one measurement section. Accordingly, it is also conceivable that the contacting device contacts the electrical conducting element at two or more contacting locations and accordingly defines two or more second measurement points defining the at least one measurement section. The contacting device may comprise at least one contact element for establishing an electrical contact between the contact element and the electrical conducting element at the at least one contacting location. For this purpose, the contact element may be formed from a conducting material such as metal. The contact element may, for example, be connectable or connected at both of its ends to the above-mentioned voltage source. When the contact element is brought into contact with the electrical conducting element, for example the electrical conductor, at the contacting location, a circuit closes via the measurement section of the electrical conductor and the electrical contact, and it is possible to measure the electrical resistance present at the measurement section. The at least one contact element may, for example, be of strip-shaped form and extend along the electrical conducting element, e.g. along the entire length of the electrical conducting element. Furthermore, two or more contact elements may also be provided beside one another, e.g. running parallel in the longitudinal direction of the electrical conducting element.

The contacting device may further comprise at least one triggering element which can be positioned relative to the at least one contact element and which is configured to cause the at least one contact element to establish the electrical contact. For example, the triggering element may be arranged so as to be movable or repositionable in the longitudinal direction of the electrical conducting element (possibly also in the longitudinal direction of the contact element, depending on the shape of the contact element). A displacement of the at least one triggering element is also conceivable. The at least one triggering element may, for example, be of pin-shaped or nail-shaped form. It is conceivable that the at least one contact element is arranged at a flexible covering of the electrical conducting element in a manner spaced from the electrical conducting element and the triggering element, for example the pin-shaped triggering element, is configured to press the contact element at the at least one contacting location against the electrical conducting element. By positioning two or more triggering elements, the contact element may accordingly be pressed against the electrical conducting element at two or more contacting locations. If, for example, two or more contact elements are provided in the longitudinal direction of the electrical conducting element, the triggering element may also comprise one or more projections, with the aid of which selectively one or more of the two or more contact elements may be pressed against the electrical conducting element.

The contacting device may further comprise a positioning unit, it being possible for the triggering element to be positioned in the positioning unit to establish the electrical contact between the electrical conducting element and the contact element at the contacting location. For example, the positioning unit may extend along the electrical conducting element and comprise in the longitudinal direction a multiplicity of positioning receptacles. The positioning receptacles are each configured to receive the at least one triggering element for establishing the electrical contact. For example, the positioning receptacles may be formed as holes or as mutually opposite hole pairs, through which the triggering element, for example the pin-shaped triggering element, may be inserted and held. As a result, the contact between contact element and electrical conducting element may be established and a circuit closed along the measurement section. For example, the positioning unit may have along its longitudinal axis a multiplicity of such holes or hole pairs, in which a respective triggering element may be positioned.

According to a second aspect, an aircraft comprising at least one oxygen module mounted on board the aircraft and at least one sensor device, as is/has been described herein, is provided. The at least one oxygen module may be arranged so as to be movable, for example also displaceable, in the longitudinal direction of the aircraft.

The evaluating unit of the sensor device may be configured to derive the position of the oxygen module in the longitudinal direction of the aircraft based on the determined electrical resistance.

It is conceivable that a multiplicity of oxygen modules are arranged in the aircraft (e.g. along the longitudinal axis of the aircraft), for example one oxygen module being assigned to each seat row, e.g. in that one oxygen module is situated above each seat row. Accordingly, for each of the multiplicity of oxygen modules, a sensor device may be provided and arranged in the aircraft. For each seat row, it is possible with the aid of the sensor device, as described above, to determine the length of the measurement section and hence the position of the corresponding oxygen module in the longitudinal direction of the aircraft (of the supply duct of the aircraft). It is thereby possible to check in a simple manner whether the oxygen module of the corresponding seat row is situated at the correct position in the longitudinal direction of the aircraft. If one or more of the multiplicity of oxygen modules are not correctly positioned, this or these oxygen modules may be accordingly repositioned and the new position may then be determined again in a simple manner by the associated sensor device.

It is conceivable that the sensor device is arranged on a closure flap of the oxygen module. In a non-triggered normal state, such a closure flap, behind which are situated the oxygen module and the oxygen masks assigned to the seats of the seat row, is closed. In the event of a drop in pressure in the cabin, e.g. the closure flap is automatically opened. For example, a device for retaining the masks in the emergency oxygen module is opened by a physical connection, for example a cord, string or lanyard connection, and the masks drop out.

The sensor device may be connected to the oxygen module via a physical connection, such as a cord, string or lanyard connection. For example, the lanyard connection may be connected on the one side to the oxygen module and on the other side to the triggering element, so that when the triggering element is positioned in the positioning device the electrical conducting element is contacted, a measurement section is defined and accordingly a changed resistance (compared with the predetermined reference resistance) is detected by the evaluating unit. From this, the evaluating unit can derive that the oxygen module is installed. By contrast, if it is ascertained that the determined electrical resistance corresponds to the reference resistance, it can be deduced from this that the oxygen module associated with the seat row is not installed or at least the triggering element is not (has not been) connected to the closure flap via the positioning unit.

The sensor device may be connected, for example, in such a manner to the at least one oxygen module via the cord, string or lanyard connection that a release (e.g. an automatic opening) of the closure flap of the oxygen module causes or occasions oxygen masks assigned to the oxygen module to drop out. As a result, the mechanical connection between oxygen module and closure flap can be reliably detected or checked.

Even though some of the above-described aspects have been described with reference to the evaluating unit or the aircraft, these aspects may also be implemented as a method or as a computer program which carries out the method. For example, the evaluating unit may comprise, for carrying out at least some of the above-described aspects, a computer program with program code means which, when it is loaded in a computer or a processor (for example a microprocessor or microcontroller), or runs on a computer or processor (e.g. a microprocessor or microcontroller), causes the computer or processor (e.g. the microprocessor or microcontroller) to carry out the above-described aspects.

BRIEF DESCRIPTION OF DRAWINGS

Preferred embodiments of the present invention are explained below with the aid of the appended schematic figures, in which:

FIG. 1b shows a schematic illustration of a part of the sensor device from FIG. 1a;

FIG. 1c is shows a schematic illustration of a detail of the sensor device from FIG. 1a;

FIG. 2b shows a schematic illustration of a front view of the sensor device from FIG. 1a in a triggered state;

FIGS. 4a to 4h shows the sensor device from FIG. 3 in different measurement configurations.

DETAILED DESCRIPTION OF EMBODIMENTS

In what follows, without being limited thereto, specific details are set out in order to provide a complete understanding of the present invention. However, it is clear to a person skilled in the art that the present invention may be used in other embodiments which may deviate from the details set out below.

It is clear to a person skilled in the art that the explanations set out below may be implemented using hardware circuits, software means or a combination thereof. The software means may be associated with programmed microprocessors or a general computer, an ASCI (Application Specific Integrated Circuit) and/or DSPs (Digital Signal Processors). Moreover, it is clear that even though the following details are described with reference to a method, the latter may also be realised in a suitable apparatus unit, a computer processor or storage connected to a processor, the storage being provided with one or more programs which carry out the method when they are executed by the processor.

Figure 1A:
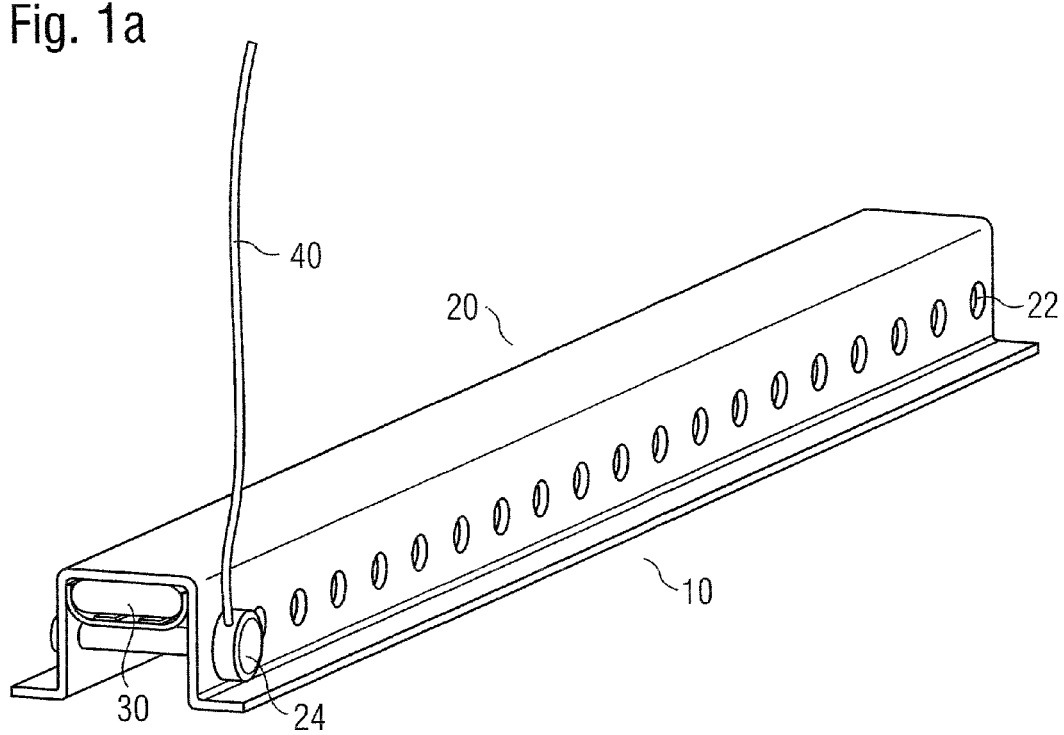
FIG. 1a shows a schematic illustration of an embodiment of a sensor device.

FIGS. 1a and 2b schematically show an embodiment of a sensor device. With reference to FIGS. 1a to 2b, mainly the electrical and mechanical components of the sensor device are described without going into detail on the functioning of the sensor device, which is explained subsequently with reference to FIGS. 3 to 4h. Therefore, the evaluating unit of the sensor device is not illustrated in FIGS. 1a to 2b. However, it is clear to a person skilled in the art that the illustrations from Figures is to 2b may be connected in a suitable manner to an evaluating unit, as is described for example with reference to FIGS. 3 to 4h.

The sensor device 10 according to the embodiment has a positioning unit 20 which comprises an at least approximately U-shaped hollow profile. In the lateral surfaces of the positioning unit 20, there are arranged in each case a multiplicity of mutually opposite holes 22 which form in each case hole pairs in the mutually opposite lateral surfaces. The holes 22 are in each case of such a diameter that a triggering element 24, illustrated with reference to the first embodiment by way of example as a pin-shaped triggering element 24, can be pushed through them. The diameter of the pin-shaped triggering element 24 is matched to the holes 22 and at one end, however, is larger in order to prevent the triggering element 24 from penetrating too far into the holes 22. On account of the enlarged diameter at the one end, the triggering element 24 may also be referred to as nail-shaped or screw-shaped. At the end of the triggering element 24 with the enlarged diameter, a lanyard cable 40 is attached. In the U-shaped hollow profile of the positioning unit 20, there is arranged an electrical conducting element 30, which can be seen in greater detail in FIG. 1b, the electrical conducting element 30 comprising, for example, either a shielding with respect to the positioning unit 20 or the positioning unit 20 being composed of a non-conducting material.

Figure 1B:
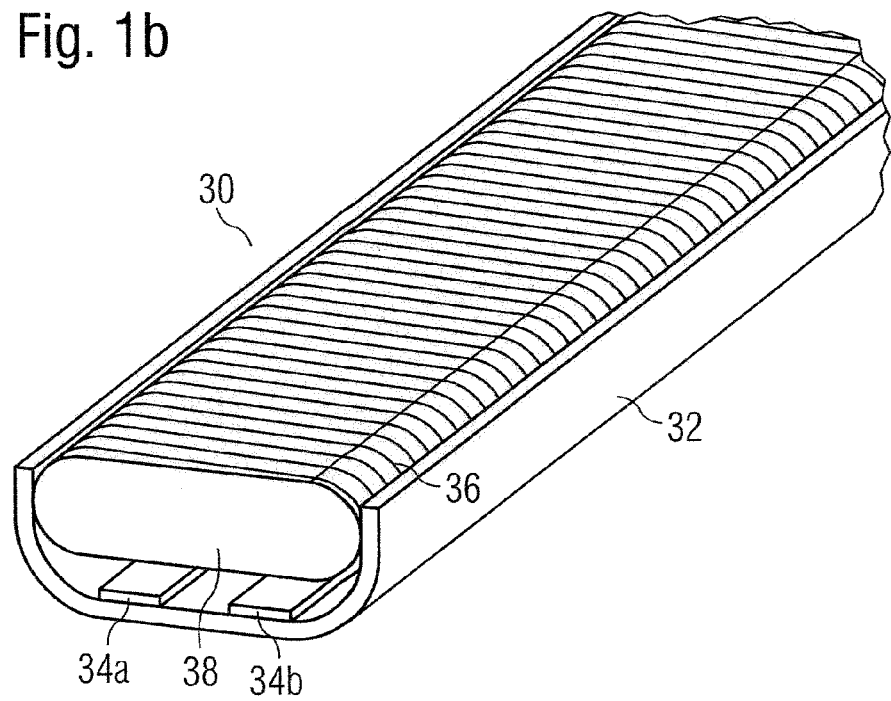
Figure 1C:
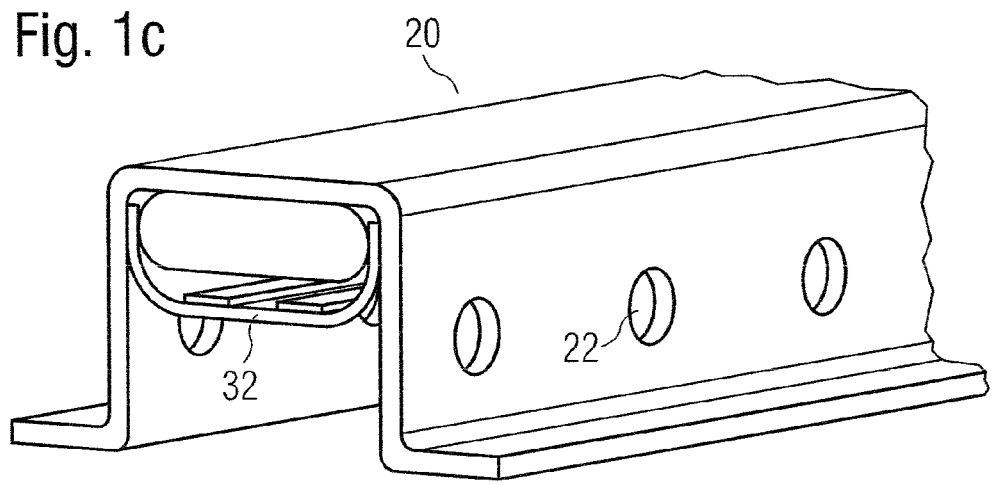
Figure 2A:
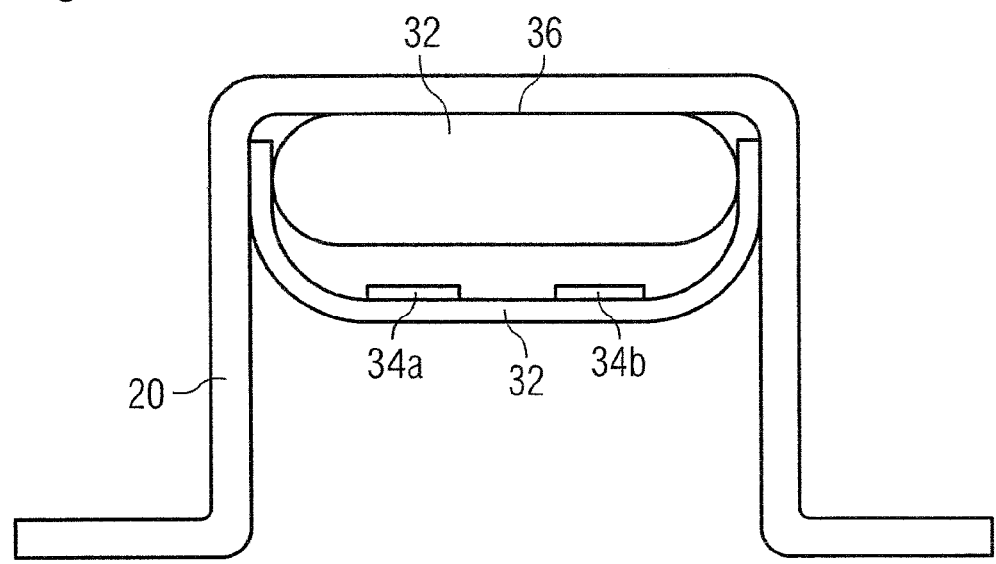
FIG. 2a shows a schematic illustration of a front view of the sensor device from FIG. 1a in a non-triggered state.

The electrical conducting element 30 comprises a base body 38 made of a non-conductive material, and an electrical conductor 36 which is wound in the form of a coil around the base body 38. For the shielding of the electrical conductor 36 from external influences, a flexible covering 32 made of an insulating material is provided. On the upper side of the flexible covering 32 facing the electrical conductor 36, there are arranged two strip-shaped contact elements 34a, 34b. Even though two strip-shaped contact elements 34a, 34b are shown by way of example in FIGS. 1a to 2b, it is also possible for only one contact element or more than two contact elements to be provided on the flexible covering 32. As the simplest variant, only a single such contact element is arranged on the covering 32. In order to increase the redundancy stepwise, the number of contact elements may be increased. In FIGS. 1b, 1c and 2a, the electrical conducting element 30 is in a non-triggered initial state.

As can be seen in FIGS. 1c and 2a, in this initial state the flexible covering 32 and the strip-shaped contact elements 34a, 34b are arranged in manner spaced from the base body 38 and hence also from the electrical conductor 36. Put another way, in the initial state according to FIG. 2a, there is no contact between the electrical conductor 36 and one or more of the two contact elements 34a, 34b. In the initial situation from FIG. 2a, there exists no closed circuit running via the electrical conductor 36 and the strip-shaped contact elements 34a, 34b. By contrast, there exists a closed circuit along the entire length of the electrical conductor 36 when, accordingly, a voltage is applied to the ends of the latter or connecting lines run to a voltage source, as will be described in more detail with reference to FIGS. 3 to 4h.

If now, as shown in FIG. 2b, the pin-shaped triggering element 24 is pushed through one of the holes 22 of the positioning unit 20 (see in this regard also FIG. 1a), the triggering element 24 presses the flexible covering 32 and hence the contact elements 34a, 34b against the electrical conductor 36 and establishes at this contacting location an electrical contact between the contact elements 34a, 34b and the electrical conductor 36. As a result, there is formed a measurement section between the end of the electrical conductor 36 as first measurement point (by way of example it is assumed that the end of the sensor device 10 and of the electrical conductor 36 lies at the rear in FIG. 1a and the beginning of the sensor device 10 and of the electrical conductor 36 lies at the front in FIG. 1a) and the contacting location as second measurement point. If a voltage is applied to one end of the electrical conductor 36 and one end of at least one of the electrical contact elements 34a, 34b, current can be conducted by the electrical conductor 36 at the contacting location onto the strip-shaped contact element(s) 34a, 34b or vice versa. This is due to the fact that, as can be seen in FIGS. 1a to 2b, the cross-section of the electrical conductor 36 is minimally small compared with the cross-section of the contact elements 34a, 34b. This means that the electrical conductor 36 has a substantially higher resistance than the contact elements 34a, 34b, i.e. the resistance of the contact elements 34a, 34b is negligibly small compared with the resistance of the electrical conductor 36. Consequently, the majority of the current or approximately the entire current is not transmitted via the electrical conductor 36 but led onto the contact element 34a and/or the contact element 34b. In the circuit formed, the evaluating unit may be arranged, as will be described with reference to FIGS. 3 to 4h. Accordingly, the evaluating unit can evaluate the electrical resistance along the measurement section, as explained with reference to FIGS. 3 to 4h.

Figure 3:
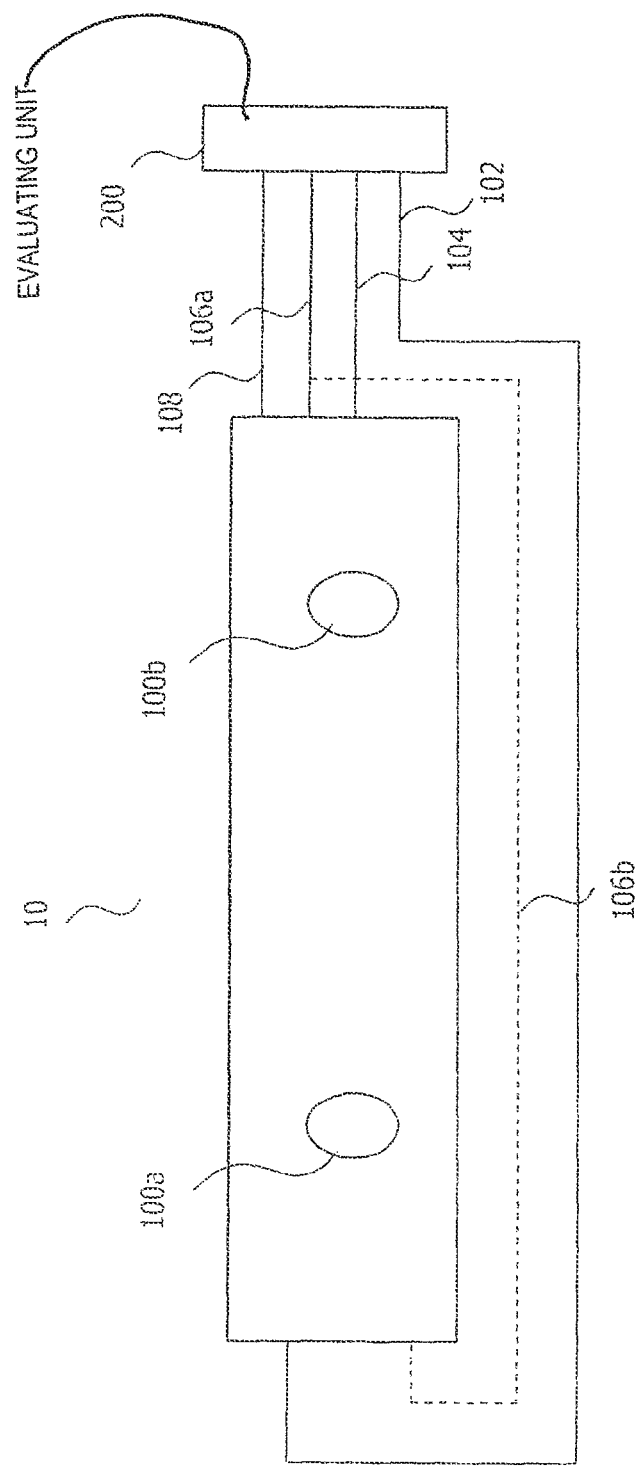
FIG. 3 shows a schematic illustration of the sensor device from FIGS. 1a to 2b according to one possible circuit arrangement having an evaluating unit of the sensor device.

FIG. 3 shows, in a greatly simplified and schematic manner, the basic construction of the sensor device 10 of FIGS. 1a to 2b according to one possible circuit arrangement having an evaluating unit 200 of the sensor device 10. In what follows, it is assumed, purely by way of example, that the beginning (the front part) of the sensor device 10 is also situated at the front in FIG. 1a. This front part of the sensor device 10 is situated, purely by way of example, on the left side in FIGS. 3 to 4h. This has the result, purely by way of example in FIGS. 3 to 4h, that the rear part of the sensor device 10 (which part is also illustrated at the rear in FIG. 1a) is connected to the evaluating unit 200. This configuration may be exactly the other way round.

As can be seen in FIG. 3, a plurality of lines 102, 104, 106a and 108 run into the evaluating unit 200. Instead of the four lines shown, it is also possible for only two lines or more than four lines to run into the evaluating unit 200. According to a first variant shown in FIG. 3, three cables, namely the lines 104, 106a and 108, run into the rear part of the sensor device 10 and only the line 102 runs into the front part of the sensor device. According to a second variant, however, one of the lines may also be run into the front part instead of into the rear part, as is shown with regard to the line 106b. For the sake of simplicity, it is assumed below that only a single strip-shaped contact element 34 is arranged on the covering 32 instead of the two strip-shaped contact elements 34a, 34b.

The circles in FIG. 3 symbolise, by way of example, two contacting locations 100a, 100b in a purely schematic illustration, which represent two measurement points for defining one or more measurement sections and accordingly are referred to below also alternately as measurement points 100a, 100b The measurement points 100a, 100b are formed, in the example shown in FIGS. 3 to 4h, by establishing a contact between the electrical conductor 36 and the electrical contact element 34 at the positions corresponding to the measurement points by inserting two triggering elements 24 at precisely these positions. The measurement points 100a, 100b define one or more measurement sections, along which the electrical resistance is measured by the evaluating unit 200. It will be understood that only one of the measurement points 100a, 100b is sufficient to define a measurement section or else more than two measurement points 100a, 100b may be provided. One of the measurement points 100a, 100b is sufficient, for example, when the front or rear end of the electrical conductor 36 is used as the other measurement point. One of the lines 102, 104, 106a (or 106b), 108 may be connected selectively to the front end of the strip-shaped contact element 34 and another of the lines 102, 104, 106a (or 106b), 108 may be connected selectively to the rear end of the strip-shaped contact element 34. Another of the lines 102, 104, 106a (or 106b), 108 may be connected selectively to the front end of the electrical conductor 36 and the last of the lines 102, 104, 106a (or 106b), 108 may be connected selectively to the rear end of the electrical conductor 36.

In FIGS. 4a to 4h, the contact element 34 which extends in the longitudinal direction of the control device 10 can be seen schematically. Furthermore, an electrical conductor 36 is indicated, which conductor may be configured in the same manner as the electrical conductor 36 from Figures is to 2b. FIGS. 4a to 4h show, by way of example, one possible circuit arrangement, in which the line 102 is connected to the front end of the electrical conductor 36, the line 104 is connected to the rear end of the electrical conductor 36, the line 106 is connected to the front end of the contact element 34 and the line 108 is connected to the rear end of the contact element 34. Purely by way of example, it can be seen in FIGS. 4a to 4h how the electrical conductor 36 may contacted at two measurement points (contacting locations) 100a, 100b by the contact element 34. It is likewise conceivable that the electrical conductor 36 may be contacted only at one variable contacting location 100a, 100b by the contact element 34, and the measurement section is defined by this variable contacting location 100a, 100b and a fixed reference point, e.g. the front or rear end of the electrical conductor 36. It is likewise conceivable that more than two measurement points may be provided, which points may each be established by one and the same contact element 34 or further contact elements.

The functioning of the sensor device 10 will now be explained with the aid of FIGS. 4a to 4h.

As can be seen in FIGS. 4a to 4h, the contacting locations and hence the measurement points 100a, 100b define at least one measurement section from the measurement sections x1, x2, x3, as will be explained below. In all the FIGS. 4a to 4h, the dashed lines represent current-carrying lines. The continuous lines are, accordingly, without current. Which lines 102, 104, 106, 108 are used for measurement is defined by control logic in the evaluating unit 200 in dependence on the measurement to be carried out.

An initial state, as may be used, for example, for calibrating the evaluating unit 200, is shown in FIG. 4a. This means that FIG. 4a represents a kind of check measurement which may be carried out, for example, during the calibration of the evaluating unit 200. In the check measurement, the contact element does not contact the electrical conductor 36 at any of the measurement points 100a, 100b, there is no triggering element 24 arranged in the positioning unit 30. In FIG. 4a, the lines 102 and 104 serve, by way of example, for the measurement, i.e. the evaluating unit 200 applies a voltage to these lines, so that a current flows via the line 102 onto the electrical conductor 36 and finally via the line 104 into the evaluating unit 200. The current flows over the entire length of the electrical conductor 36, since the contact element 34 does not contact the electrical conductor 36 at any location. If it is assumed in simplified terms that the resistance of the lines 102, 104 is negligibly small compared with the resistance of the electrical conductor 36, the resistance value of the entire conductor 36 is determined by the check measurement and saved (stored) in the evaluating unit 200. Otherwise, the resistance present along the lines 102, 104 has to be taken into account in this and subsequent measurements as well. In the embodiment, the cross-section, the length and the material of the lines 102 to 108 are chosen, however, such that the resistance of the lines 102 to 108 is negligibly small compared with the resistance of the electrical conductor 36. After the check measurement, a reference resistance or reference resistance value is therefore known in the evaluating unit 200, namely the resistance of the entire conductor 36.

In FIG. 4b, by way of example, the line pair 106, 108 is selected by the evaluating unit 200 as the line pair for the measurement and is supplied with current. Here, too, no triggering element 24 is inserted into the positioning unit 20, i.e. here too there is no contact between the electrical conductor 36 and the contact element 34. The current accordingly flows via the line 106 to the almost resistanceless contact element 34 and via the line 108 back to the evaluating unit 200. If it is assumed in simplified terms that not only the contact element 34 but also the lines 106, 108 have a negligible small resistance, the evaluating unit 200 measures almost no resistance (resistance approximately 0; short-circuit state). If the lines 106, 108 have a resistance, only the resistance of the lines 106, 108 is measured by the evaluating unit 200.

In FIG. 4c, it can be seen how the lines 102, 106 are selected for the measurement by the evaluating unit 200, i.e. the evaluating unit 200 applies a voltage to these lines 102, 106. Furthermore, a triggering element 24 is positioned in the positioning unit 20 at the contacting location corresponding to the measurement point 100a, since the oxygen module is situated at a corresponding or the same position in the longitudinal direction of the aircraft. As a result, the current flows from the conductor 102 firstly onto the electrical conductor 36. Since, however, there is a contact between the contact element 34 and the electrical conductor 36 at the measurement point 100a, on account of the substantially smaller resistance of the contact element 34 the current does not flow on into the evaluating unit 200 via the electrical conductor 36 but via the contact element 34 and the line 106. As a result, the measurement section x1 defined by the measurement point 100a, to be more precise the resistance present there, is measured by the evaluating unit 200. The measurement section x1 is defined by the beginning of the electrical conductor 36 and the measurement point 100a. From the quotient of the resistance along the measurement section x1 and the total resistance along the electrical conductor 36, i.e. the reference resistance, the evaluating unit 200 can determine the length of the measurement section x1 (by multiplying the quotient by the length of the electrical conductor 36). From the length of the measurement section x1, the evaluating unit 200 can deduce at which point in the longitudinal direction of the sensor device 10 and hence in the longitudinal direction of the aircraft the contacting location and hence also the oxygen module are situated.

FIG. 4d illustrates how the same measurement section x1 can be measured in an alternative manner. Here, the evaluating unit 200 selects the lines 102 and 108 and applies a voltage to these lines. The current flows via the line 102 into the electrical conductor 36 and on account of the contact existing at the measurement point 100a into the contact element 34 and from there via the line 108 into the evaluating unit 200. The evaluating unit 200 now measures the same resistance as in FIG. 4c, namely the resistance along the measurement section x1, and can thereby determine the position of the oxygen module.

FIGS. 4e and 4f now show how the measurement section x3 can be measured in a different manner. The measurement section x3 is defined by the contact element 34 contacting the electrical conductor 36 at the contacting location corresponding to the measurement point 100b (by inserting the triggering element 24 at the corresponding location into the positioning unit 20), because, for example, the oxygen module is arranged at the same location 100b in the longitudinal direction of the aircraft (or at a corresponding location). The measurement section x3 is therefore defined by the end of the electrical conductor 36 and the measurement point 100b. The evaluating unit 200 now applies a voltage to the lines 104 and 108 in FIG. 4e. As a result, current flows via the line 104 into the electrical conductor 36, from there into the contact element 34 and back into the evaluating unit 200 via the line 108. In FIG. 4f, a voltage is applied to the lines 104 and 106, so that the current flows via the line 104 through the electrical conductor 36, the contact element 34 and via the line 106 into the evaluating unit 200. Both times, the evaluating unit 200 measures the resistance along the measurement section x3 (thereby knows the length of the measurement section x3) and can thereby determine at which location the contact is arranged and hence also at which location the oxygen module is arranged.

FIG. 4g illustrates how the part of the electrical conductor 36 formed from the measurement sections x2 and x3 and hence the resistance along the measurement section x1 can be derived. The triggering element 24 is placed at the contacting location corresponding to the measurement point 100a, since the oxygen module is arranged at the corresponding location. The evaluating unit 200 applies a voltage to the lines 104, 108, so that the current flows via the line 104, the electrical conductor 36, via the contacting location 100a onto the contact element 34 and the line 108 finally into the evaluating unit 200. The measured resistance corresponds to the resistance present along the measurement section x2+x3. By obtaining the difference between reference resistance and the determined resistance, it is possible to derive the resistance along the measurement section x1. As a result, the evaluating unit can determine the length of the measurement section x1 and therefore also the contacting location and the position of the oxygen module.

In FIG. 4h, the triggering element 24 is positioned in the positioning unit 20 at the same contacting location 100a, but the evaluating unit 200 applies a voltage to the lines 102 and 108. As a result, current flows via the line 102, the electrical conductor 36, the contacting location 100a, the contact element 34 and the line 108 into the evaluating unit 200. The evaluating unit 200 measures the resistance along the measurement section x1, from this derives the length x1 and from this deduces at which location the oxygen module is positioned.

Even though the current has always flowed clockwise in FIGS. 4a to 4h, purely by way of example, the current may also flow anticlockwise if the voltage is applied accordingly the other way round.

Figure 5:
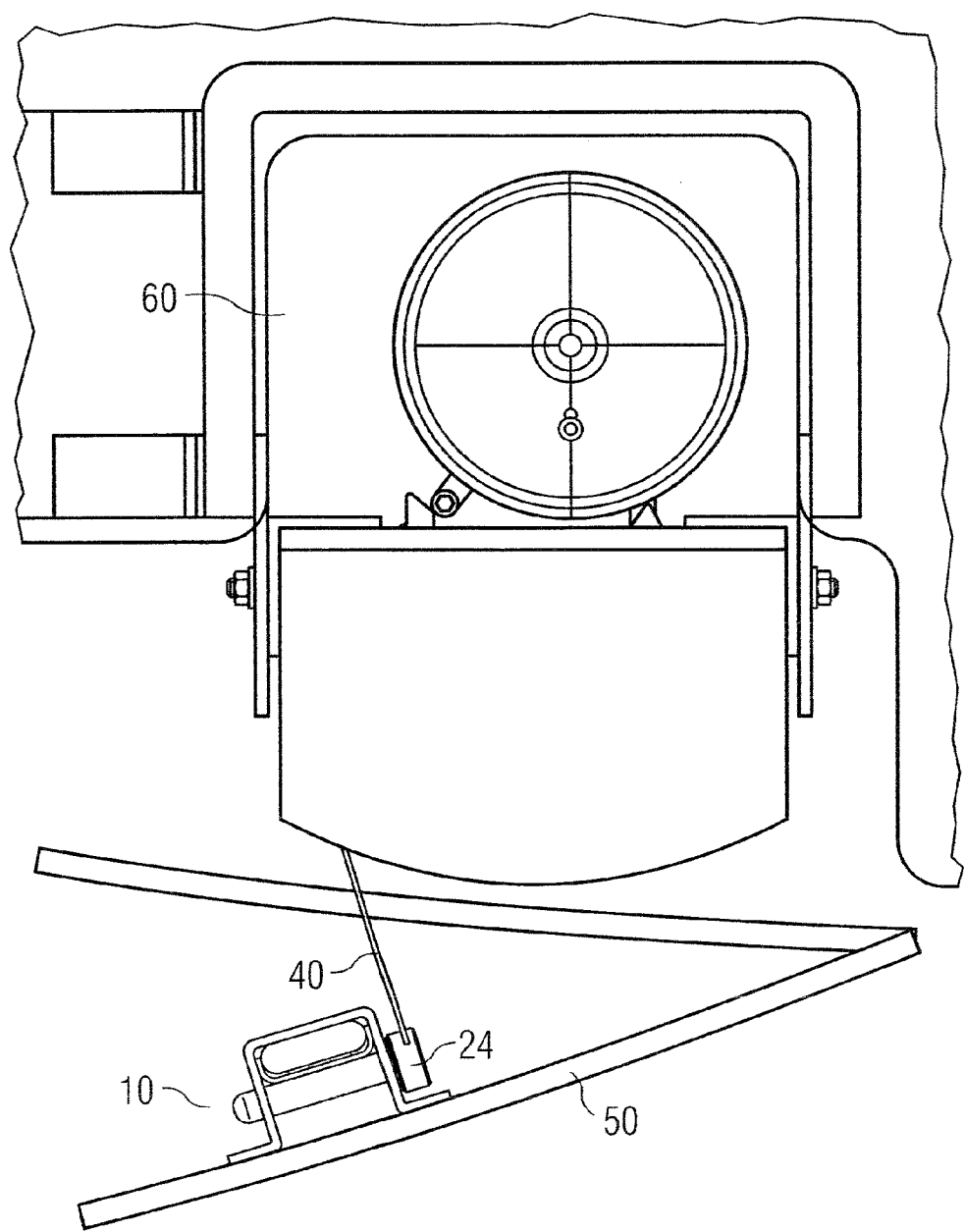
FIG. 5 shows the sensor device from FIG. 1a in the installed state.

FIG. 5 illustrates, by way of example, how the sensor device 10 can be installed in an aircraft. As can be seen, the sensor device 10 is arranged on a closure flap 50 of the oxygen module. The sensor device 10 is connected to the oxygen module 60 via the lanyard connection 40. As a result of the fact that the lanyard connection 40 is arranged on the triggering element 24, in the inserted state of the triggering element 24, a resistance different from the reference resistance is measured. From this, the evaluating unit 200 recognises that the triggering element 24 is inserted and hence also the oxygen module is installed. It is thereby checked in a simple manner whether the oxygen module 60 is correctly installed. The physical connection between the oxygen module 40 and the closure flap 50 ensures that in the event of a drop in pressure in the cabin (e.g. in an emergency) and the ensuing opening of the closure flap 50, the sheet surrounding the oxygen masks is torn out and the oxygen masks drop out. Thus, correct connection between sensor device 10 and oxygen module further ensures that the oxygen masks are released.

The invention claimed is:

1. A sensor device for an oxygen module mountable on board an aircraft, the sensor device comprising:
   an electrical conducting element;
   a defining device for defining at least one measurement section, assigned to the oxygen module, on the electrical conducting element; and
   an evaluating unit for determining an electrical resistance present along the at least one measurement section, the evaluating unit further being configured to ascertain, based on the determined electrical resistance, whether the oxygen module is present, and the evaluating unit further being configured to ascertain that the oxygen module is present when the determined electrical resistance is less than a predetermined reference resistance by at least a pre-set deviation from the predetermined reference resistance.

2. The sensor device according to claim 1, the evaluating unit further being configured to derive the position of the oxygen module by comparing the determined electrical resistance with the reference resistance.

3. The sensor device according to claim 1, the evaluating unit being configured to derive the position of the oxygen module from the quotient from the determined electrical resistance and the reference resistance.

4. The sensor device according to claim 1, the defining device comprising a contacting device for contacting the electrical conducting element at at least one contacting location, the at least one contacting location being assigned to the oxygen module, and defining the at least one measurement section on the electrical conducting element.

5. The sensor device according to claim 4, the contacting device comprising at least one contact element for establishing an electrical contact between the contact element and the electrical conducting element at the at least one contacting location.

6. The sensor device according to claim 5, the at least one contact element being of strip-shaped form and extending along the electrical conducting element.

7. The sensor device according to claim 5, the contacting device further comprising at least one triggering element which can be positioned relative to the at least one contact element and which is configured to cause the at least one contact element to establish the electrical contact.

8. The sensor device according to claim 7, the at least one contact element being arranged on a flexible covering of the electrical conducting element in a manner spaced from the electrical conducting element and the triggering element being configured to press at least one of the at least one contact element at the at least one contacting location against the electrical conducting element.

9. The sensor device according to claim 7, the contacting device further comprising a positioning unit, it being possible for the triggering element to be positioned in the positioning unit to establish the electrical contact between the electrical conducting element and the at least one contact element at the contacting location.

10. The sensor device according to claim 9, the positioning unit extending along the electrical conducting element and comprising in the longitudinal direction a multiplicity of positioning receptacles which are each configured to receive the triggering element for establishing the electrical contact.

11. An aircraft comprising at least one oxygen module mounted on board the aircraft and at least one sensor device according to claim 1.

12. An aircraft according to claim 11, the at least one oxygen module being arranged so as to be movable in the longitudinal direction of the aircraft and the evaluating unit of the at least one sensor device being configured to derive the position of the oxygen module in the longitudinal direction of the aircraft based on the determined electrical resistance.

13. The aircraft according to claim 11, the at least one sensor device being arranged on a closure flap of the oxygen module.

14. The aircraft according to claim 11, the at least one sensor device being connected to the at least one oxygen module via a cord, string or lanyard connection.

15. The aircraft according to claim 14, the sensor device being connected in such a manner to the at least oxygen module via the cord, string or lanyard connection that a release of the closure flap causes oxygen masks assigned to the oxygen module to drop out.

* * * * *